(12) United States Patent
Chen et al.

(10) Patent No.: US 7,582,763 B2
(45) Date of Patent: Sep. 1, 2009

(54) ENANTIOSELECTIVE PROCESS

(75) Inventors: Frank Xing Chen, Plainsboro, NJ (US); Yee-Shing Wong, Florham Park, NJ (US); Feng Liang, Monmouth Junction, NJ (US); Marc Poirier, Edison, NJ (US); George Wu, Basking Ridge, NJ (US)

(73) Assignee: Schering Corporation, Kenilworth, NJ (US)

( * ) Notice: Subject to any disclaimer, the term of this patent is extended or adjusted under 35 U.S.C. 154(b) by 563 days.

(21) Appl. No.: 11/287,041

(22) Filed: Nov. 23, 2005

(65) Prior Publication Data
US 2006/0074241 A1    Apr. 6, 2006

Related U.S. Application Data

(62) Division of application No. 10/676,212, filed on Oct. 1, 2003, now Pat. No. 7,049,440.

(60) Provisional application No. 60/418,806, filed on Oct. 15, 2002, provisional application No. 60/415,673, filed on Oct. 3, 2002.

(51) Int. Cl.
*C07D 221/22* (2006.01)
(52) U.S. Cl. .......................................... 546/93
(58) Field of Classification Search ............... 546/93
See application file for complete search history.

(56) References Cited

U.S. PATENT DOCUMENTS 6,426,352 B1 *   7/2002   Njoroge et al. .............. 514/290
6,576,639 B1 *   6/2003   Doll et al. ................... 514/290

* cited by examiner

*Primary Examiner*—D. Margaret Seaman

(57) ABSTRACT

An enantioselective process for preparing intermediates useful in the preparation of the chiral tricyclic compound of formula I

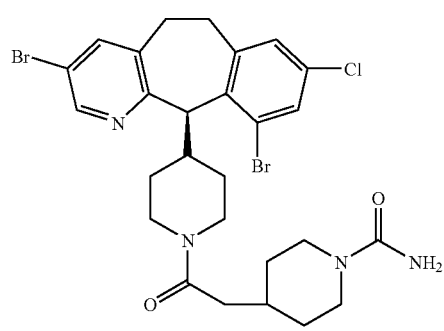

is disclosed.

4 Claims, No Drawings

ENANTIOSELECTIVE PROCESS

CROSS REFERENCE TO RELATED APPLICATIONS

This application is a divisional of application Ser. No. 10/676,212 filed on Oct. 1, 2003, which in turn claims the benefit of U.S. Provisional Application Ser. No. 60/415,673, filed Oct. 3, 2002, and U.S. Provisional Application Ser. No. 60/418,806, filed Oct. 15, 2002.

BACKGROUND OF THE INVENTION

This invention provides an enantioselective process for preparing intermediates useful in the preparation of the chiral tricyclic compound of formula I

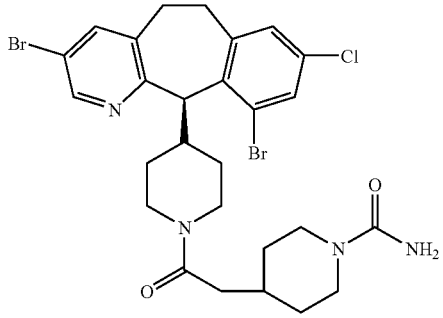

I

U.S. Pat. Nos. 5,760,232, 5,874,442, 5,719,148, 5,998,620, and 6,372,909 disclose processes for the preparation of the tricyclic compound of formula I, and its use as an inhibitor of farnesyl protein transferase inhibitor. U.S. Pat. No. 6,307,048 discloses a multistep process for preparation of the compound of formula I. There is a need for a shorter, more efficient process for the chiral tricyclic compound of formula I.

SUMMARY OF THE INVENTION

The present invention also provides an enantioselective process of preparing a compound represented by formula VI:

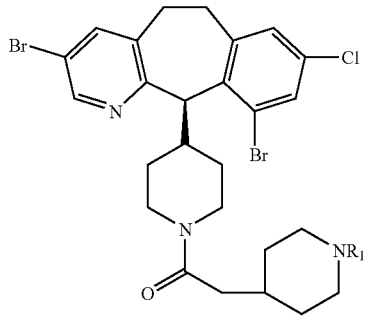

VI wherein $R_1$ is H or a protecting group;
35265 which comprises contacting a compound represented by formula V

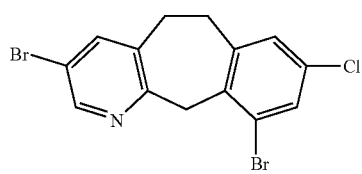

V in an inert organic solvent with at least about an equivalent amount of each of:

(i) a chiral amino alcohol represented by the formula XI

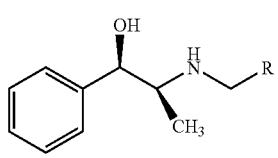

XI wherein R is an aryl, alkylaryl, alkoxylary, arylaryl, heteroarryl, or polycyclic aryl group or formula XII

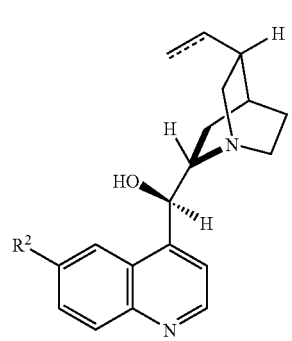

XII wherein in formula XII, the dotted line represents an optional second bond and wherein $R^2$ is selected from alkoxy, alkyoxyalkyoxy, aryloxy, arylalkoxy, and $NR^A R^B$, wherein $R^A$ and $R^B$ is independently alkyl or aryl, and $R^2$ is optionally substituted by one or more alkoxy groups;

(ii) a compound represented by formula X

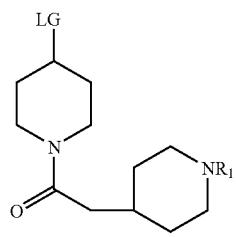

X wherein LG is a leaving group and $R_1$ is H or a protecting group, (iii) an organic ether or amine additive or mixtures thereof to form a reaction mixture; where amine is an alkylamine, arylamine, alkylarylamine, or arylalkylamine.

then adding to the reaction mixture at least about an equivalent amount of a non-nucleophilic strong base in an organic solvent, and optionally adding an effective amount of water or a $C_1$-$C_3$ alcohol to produce the compound represented by formula VI.

The present invention also provides a process for the preparation of a compound represented by formula V

V which comprises (1) contacting a compound represented by formula IIA or IIB or a mixture of IIA and IIB

IIA

IIB with at least about an equivalent amount of phosphorous acid in the presence of at least catalytic equivalent amounts of an alkali iodide or iodine and hydrobromic acid in water to form a reaction mixture, and then adding to the resulting reaction mixture a at least about an equivalent amount of hypophosphorous acid to form a compound represented by formula IIIA or IIIB or mixture of the compounds represented by formula IIIA and IIIB

IIIA

IIIB (2) contacting the resulting compounds represented by formula IIIA and IIIB or a single isomer with at least about an equivalent amount of bromine in the presence of an organic acid and a lower alkanol to form a compound represented by formula IVA or IVB or a mixture of compounds represented by formula IVA and IVB

IVA

IVB

The present invention also provides a process for the preparation of a compound represented by formula I

I which comprises contacting a compound of formula VI wherein $R_1$ is H

VI with an equivalent amount of sodium cyanate (NaOCN) in a water miscible organic solvent comprising an effective amount of water to form the compound of formula I.

DETAILED DESCRIPTION OF THE INVENTION

As used herein, the term "alkyl" means straight or branched hydrocarbon chain groups having 1 to 6 carbon atoms.

As used herein, the term "halo" means fluoro, chloro, bromo or iodo.

As used herein, the term "alkoxy" means $C_1$-$C_6$ alkoxy including methoxy and ethoxy, n-propoxy, isopropoxy, n-, iso- and tert-butoxy, n-, iso-, sec- and neo-pentyl; methoxy and ethoxy are preferred.

As used herein, the term "aryl" refers to a carbocyclic group having at least one aromatic ring. Typical aryl groups include phenyl and 1- or 2-naphthyl.

As used herein, the term "aryloxy" refers to an aryl group having the formula AR-O—, wherein AR is aryl and O is divalent oxygen. Typical aryloxy groups include phenoxy, and 1- or 2-naphthoxy.

As used herein, the term "alkylaryl" refers to an aryl group having one to five alkyl groups. Typical alkylaryl groups include 2-, 3- or 4-methylphenyl, 2-, 3- or 4-ethylphenyl, 2,3-, 3,5-, 2,6- and 3,6-dimethylphenyl, 2,4,6-trimethylphenyl As used herein, the term "arylaryl" refers to an aryl group having at least one aryl group. Typical arylaryl groups include biphenyl, and phenyl-substituted naphthyl, such as 3-phenyl [1- or 2-naphthyl]

As used herein, the term "heteroaryl" refers to an aryl group having one or more heteroatoms in the aromatic rings. Heteroaryl represents cyclic aromatic groups of 5 or 6 atoms or bicyclic groups of 11 to 12 atoms having 1 or 2 heteroatoms independently selected from O, S or N, said heteroatom(s) interrupting a carbocyclic ring structure and having a sufficient number of delocalized pi electrons to provide aromatic character, provided that the rings do not contain adjacent oxygen and/or sulfur atoms. For 6-membered heteroaryl rings, carbon atoms can be substituted by $R^9$, $R^{10}$ or $R^{11}$ groups. Nitrogen atoms can form an N-oxide. All regioisomers are contemplated, e.g., 2-pyridyl, 3-pyridyl and 4-pyridyl. Typical 6-membered heteroaryl groups are pyridyl, pyrimidinyl, pyrazinyl, pyridazinyl and the N-oxides thereof. For 5-membered are furyl, thienyl, pyrrolyl, thiazolyl, isothiazolyl, imidazolyl, pyrazolyl and isoxazolyl. 5-Membered heteraryl rings are furyl, thienyl, pyrrolyl, thiazolyl, isothiazolyl, imidazolyl, pyrazolyl and isoxazolyl. 5-Membered rings having one heteratom can be joined through the 2- or 3-position; 5-membered rings having two heteratoms are preferably joined through the 4-position. Bicyclic groups typically are benzo-fused ring systems derived from the heteroaryl groups named above, e.g. quinolyl, phthalazinyl, quinazolinyl, benzofuranyl, benzothienyl and indolyl.

As used herein, the term "polycyclic aryl group" refers to an aryl group having more than two aromatic rings such as anthracene.

As used herein, the term "ee" as used herein represents the percentage obtained by subtracting the amount of the S-enantiomer from the R-enantiomer, and dividing by the sum of the amount of R-enantiomer and S-enantiomer: e.e. %=100×(R-enantiomer–S-enantiomer)/(R-enantiomer+S-enantiomer). The compound of formula I produced in accordance with the process of the present invention has an ee of >98%, i.e., containing less than 1% of the S-enantiomer.

Non-limiting examples of leaving groups, ("LG"), include sulfonates (e.g., mesylate, tosylate, closylate (para-chloro tosylate), and brosylate (para-bromo tosylate)), phosphates (e.g., alkyl phosphates, such as diethyl phosphate), benzoates, and halides. Preferably, the leaving group, LG, is a sulfonate, more preferably, mesylate or tosylate, and most preferably mesylate.

The protecting group may be any group suitable for protecting the nitrogen atom of the piperidine ring. Non-limiting examples of protecting groups include sulfonates, and acyl groups, e.g., tert-butoxycarbonyl (t-Boc),

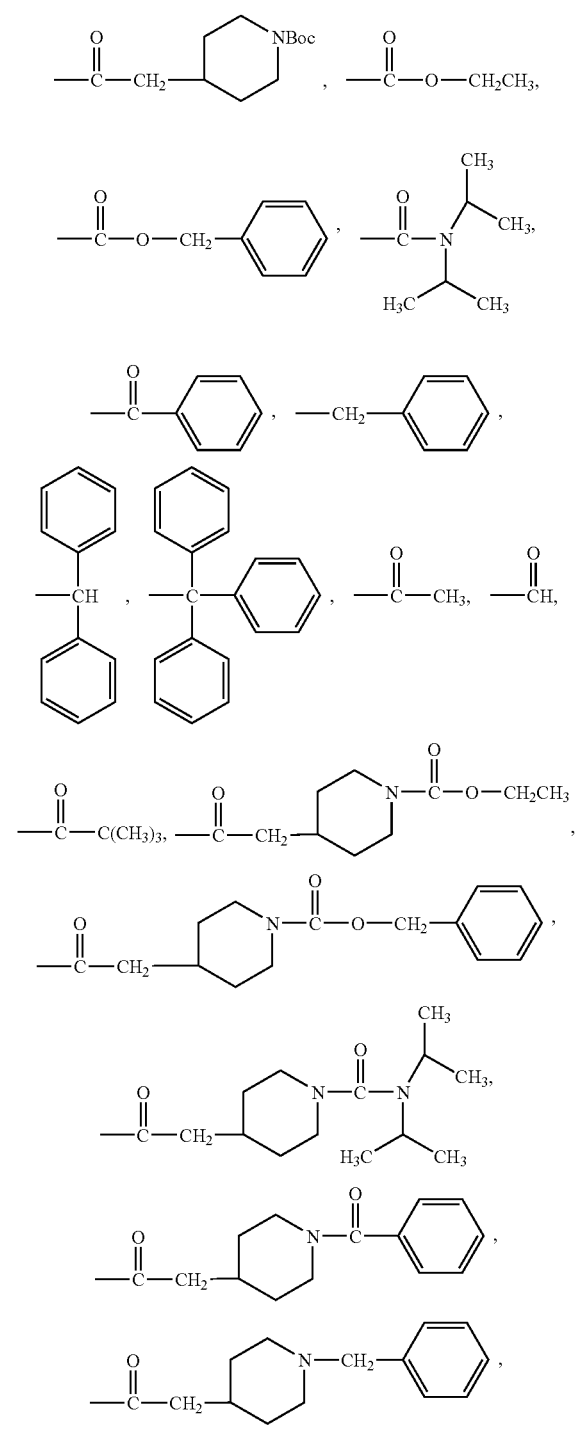

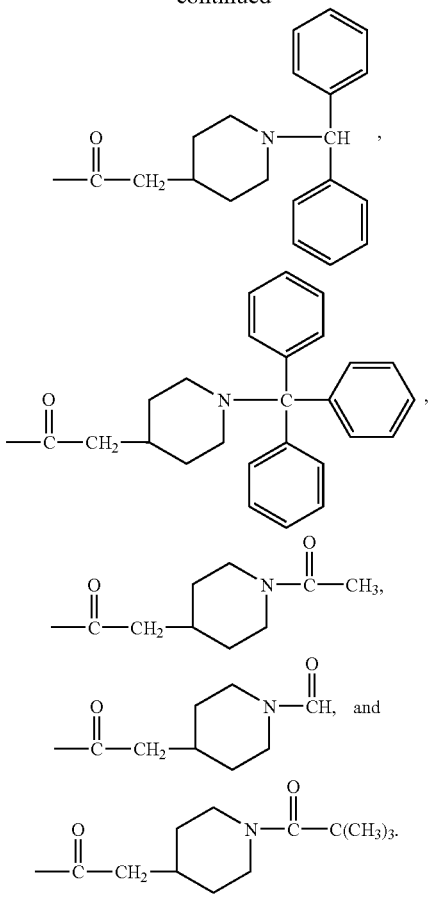

Preferably, the protecting group is an acyl group, and more preferably is tert-butoxycarbonyl (t-Boc).

Examples of suitable non-nucleophilic strong bases include, but are not limited to, the lithium bases, such as lithium diisopropylamide (LDA), lithium N-butyl, N-phenyl amide, lithium N-ethyl, N-phenyl amide, lithium 2,2,6,6-tetramethyl-piperidine, 1-lithium 4-methylpiperazide, 1,4-dilithium piperazide, lithium bis(trimethylsilyl)amide, sodium bis(trimethylsilyl)amide, potassium bis(trimethylsilyl)amide, isopropyl magnesium chloride, phenyllithium, phenyl magnesium chloride, lithium diethylamide, and potassium tert-butoxide. Preferably, the non-nucleophilic strong base is lithium diisopropylamide (LDA), lithium N-butyl, N-phenyl amide, lithium N-ethyl, N-phenyl amide, lithium bis(trimethylsilyl)amide and more preferably the non-nucleophilic strong base is lithium diisopropylamide or lithium N-ethyl, N-phenyl amide, lithium bis(trimethylsilyl)amide and most preferably the non-nucleophilic strong base are lithium bis(trimethylsilyl)amide and lithium diisopropylamide.

The term "organic amine or ether additive" as used herein means an alkyl ether, an alky amine or an aryl amine, and mixtures thereof. Examples of suitable alkyl ethers include, but are not limited to, lower alkyl ethers, e.g., diisopropyl ether, isopropyl methyl ether, isopropyl ethyl ether, isobutyl methyl ether, isobutyl ethyl ether tert-butyl methyl ether, and tert-butyl ethyl ether. Examples of suitable alkyl amines include, but are not limited to, mono-, di- and trialkyl amines, such as, isopropylamine, isobutylamine, di-isopropylamine, tetramethylethylenemdiamine ("TMEDA"), and tert-butyl amine. Examples of suitable aryl amines include, but are not limited to, aniline, 2,6-dimethylaniline, and 1- and 2-naphthyl amine, N-alkyl anilines, e.g., N-ethylaniline, N-isopropylaniline, N-butylaniline, N-arylanilines, e.g., N-phenyl, N-benzyl amine, N-phenyl(1-naphthyl amine), and N-phenyl (2-naphthyl amine), N,N-dialkyl anilines, e.g., methyl isopropylaniline, N,N-dimethylaniline, 2-isopropylaniline. Use of 2-isopropylaniline or N-N-phenyl(1- or, 2-naphthyl amine) is preferred; the use of 2-isopropylaninline is more preferred.

The term "chiral organic acids", as used herein includes, but is not limited to, N-acetyl-L-phenylalanine, N-α-(tert-butoxycarbonyl)-L-asparagine, di-p-toluoyl-L-tartaric acid, N-(tert-butoxycarbonyl)-L-proline, (S)-(–)-2-hydroxy-3,3-dimethyl-butyric acid and (1R)-(+)-camphanic acid. Use of N-acetyl-L-phenylalanine or N-α-(tert-butoxycarbonyl)-L-asparagine is preferred; the use of N-α-(tert-butoxycarbonyl)-L-asparagine is more preferred.

The chiral organic acid is used to form an acid addition salt of the compound of formula VI wherein $R_1$ is H. Crystallization of the so-formed acid addition salt in ethanol-water solvent (See Example 6 of U.S. Pat. No. 6,307,048) further enhances the enantiomeric excess ("ee") of VI wherein $R_1$ is H to greater than 98% ee, preferably greater than 99% ee, more preferably greater than 99.5% ee.

The amount of chiral organic acid used to form an acid addition salt of the compound VI is at about 0.0 to about 2.0 equivalents, preferably about 0.5 to about 1.4 equivalents, more preferably about 0.5 to about 1.2 equivalents.

The chiral amino alcohol is a norephedrine-based derivative represented by the formula XI below.

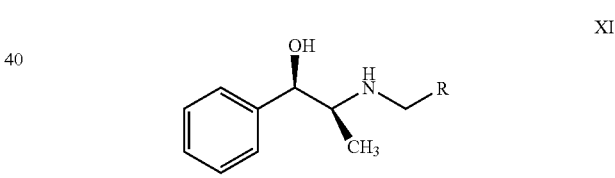

XI

The chiral amino alcohol of formula XI may be prepared by the procedure of Preparative Example A in U.S. Pat. No. 6,307,048. Non-limiting examples of chiral amino alcohols of formula XI include 3-methoxybenzyl-norephedrine, 3,5-dimethoxybenzyl-norephedrine, 3,4,5-trimethoxybenzyl-norephedrine, and 2-methoxy-1-naphthalene-norephedrine. 3,5-Dimethoxybenzyl-norephedrine, 3,4,5-trimethoxybenzyl-norephedrine are preferred. 3,4,5-trimethoxybenzyl-norephedrine, XI, is more preferred.

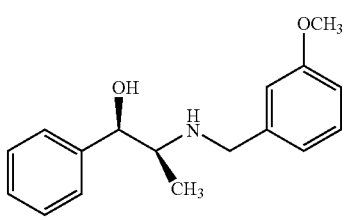

XIA

-continued

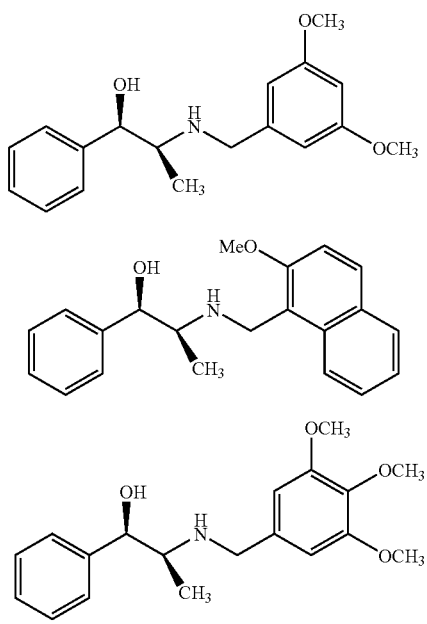

XIB

XIC

XI or a compound represented by the formula XII

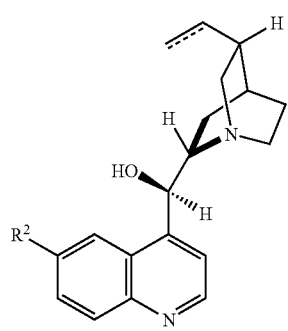

XII herein the dotted line represents an optional second bond and wherein $R^2$ is selected from alkoxy, alkoxyalkyoxy, aryloxy, arylalkoxy, or $NR^A R^B$, wherein $R^A$ and $R^B$ is independently alkyl or aryl, and $R^2$ is optionally substituted by one or more alkoxy groups.

The term "alkoxy" means $C_1$-$C_6$ alkoxy including methoxy and ethoxy, propoxy, isopropoxy, n-, iso- and tert-butoxy, n- iso-, sec- and neo-pentyl; methoxy and ethoxy are preferred.

The term "alkoxyalkyoxy" means $C_1$-$C_6$ alkoxy $C_1$-$C_6$ alkoxy, including but not limited to, ethoxymethyloxy and methoxyethyloxy; methoxymethyloxy, and ethoxyoxyethyloxy; methoxymethyloxy and methoxyethyloxy are preferred.

The term "arylalkoxy" means aryl$C_1$-$C_6$ alkoxy, including but not limited to, phenylmethoxy, i.e., benzyl, 1- or 2-naphthylmethoxy, 1- or 2-phenylethoxy, 2-[1- or 2-naphthyl]ethoxy, 1-[1- or 2-naphthyl]ethoxy, 3-, 2-, or 1-phenylpropoxy, 3-, 2-, or 1-[1- or 2-naphthyl]propoxy, 4-, 3-, 2-, or 1-phenylbutoxy, 4-, 3-, 2-, or 1-[1- or 2-naphthyl]butoxy, 5-, 4-, 3-, 2- or 1-[1- or 2-naphthyl]pentyl, 5-, 4-, 3-, 2- or 1-phenylpentyl; benzyl, 2-phenylethoxy are preferred.

Non-limiting examples of chiral amino alcohols of formula XII include quinine, and the quinine derivatives:

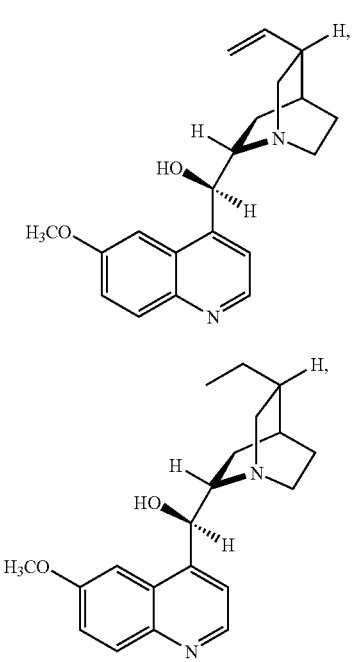

Quinine

Hydroquinine

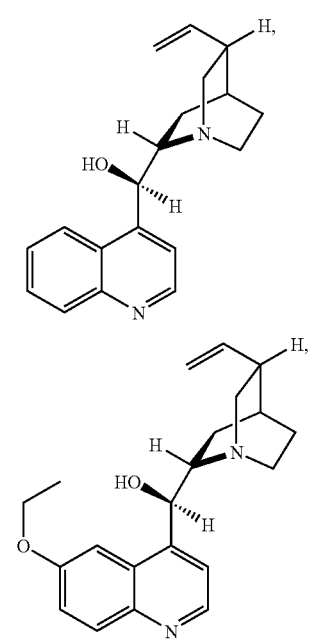

(-)-

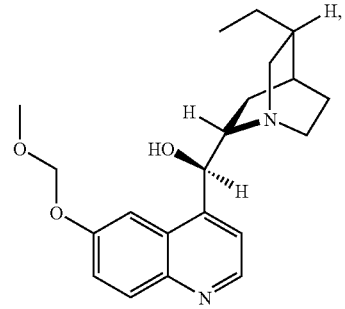

-continued
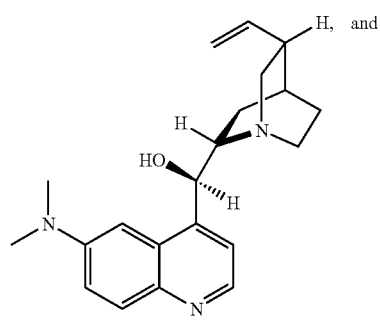
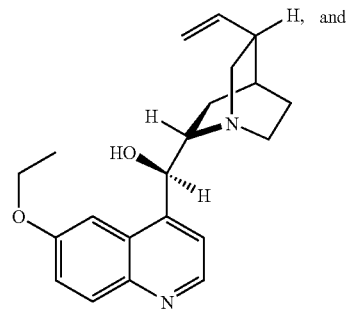
XIIA
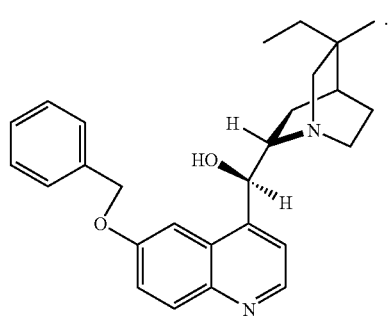
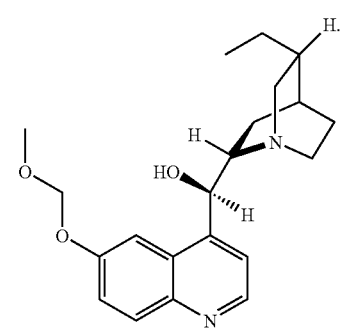
XIIB
Preferably, R² in formula XII is alkoxy. The chiral amino alcohol is most preferably selected from the compound of formula XI or quinine (XIIA), hydroquinine (XIIB),
Quinine (XIIA) is especially preferred.
Enantioselective Alkylation Step.
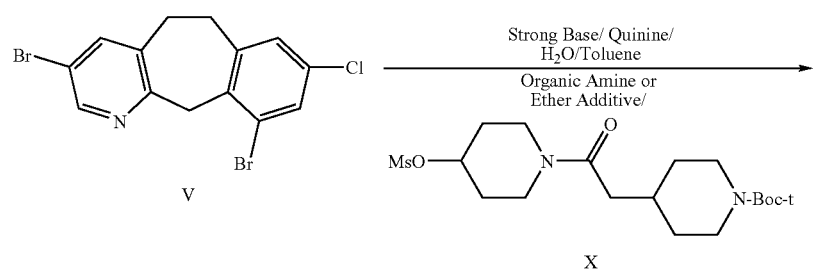
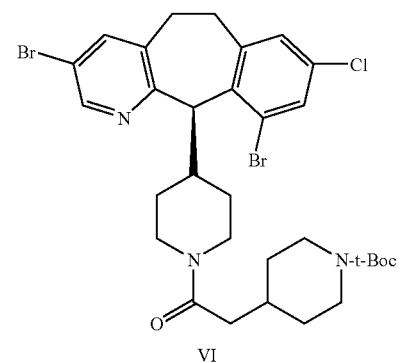

The enantioselective alkylation of the double benzylic position of compound V with a mesylate X is a much more efficient process than that disclosed in U.S. Pat. No. 6,307,048. The alkylation process of the present invention is preferably carried out such that at least one of the treatments with the non-nucleophilic strong base, reaction mixture of the chiral amino alcohol, e.g., XI or XII, the organic amine or ether additive or mixtures thereof, and the piperidine compound of formula X in an inert solvent which preferably contains water or a $C_1$-$C_3$ alcohol (e.g., methanol), most preferably, water. The equivalent amount of water or $C_1$-$C_3$ alcohol, when used, preferably ranges from 0.1 to 3.0 equivalents, more preferably 0.5 to 1.2 equivalents, most preferably 0.5 to 1.0 equivalents. The water or $C_1$-$C_3$ alcohol may be added to the tricyclic compound V prior to, or simultaneously with, the addition of the base, the chiral amino alcohol XI or XII, the organic amine or ether additive, and the piperidine compound X, or it may be added after any or all of these compounds are brought into contact with the tricyclic starting compound V.

In a particularly preferred embodiment, the following equivalent amounts are used:
(a) about 1.2 to 1.4 equivalent of the non-nucleophilic strong base, preferably about 1.3 equivalents, are added to a solution containing:
 (i) an equivalent of the compound of formula V
 (ii) about 1.0 to about 2.0 equivalents, preferably about 1.0 to about 1.5 equivalent, more preferably about 1.1 to about 1.3 equivalents of the compound of formula X, most preferably about 1.2 equivalents, and
 (iii) about 1.0 to about 4.0 equivalents, preferably about 1.2 to about 3.5 equivalents, more preferably about 1.3 to about 3.0 equivalents of the chiral amino alcohol XI or XII, most preferably about 1.5 to about 2.5 equivalents of the chiral amino alcohol XI or XII, and
 (iv) at least about about 1.0 equivalents of the organic amine or ether additive, preferably, about 1.0 to about 4.0 equivalents, preferably about 1.2 to about 3.0 equivalents, more preferably about 1.5 to about 2.5 equivalents, most preferably about 1.5 to about 2.0 equivalents or 2.0 equivalents of the organic amine or ether additive or mixtures thereof,
while maintaining the temperature of the so-formed reaction mixture at about 5° C. to about 50° C., preferably about 10° C. to about 45° C., more preferably about 15 to about 25° C.;
(b) the mixture from step (a) is cooled to about 0° C. to about 10° C., preferably about 0° C. to about 5° C., and about 0.1 to about 3.0 equivalents of water, preferably about 0.5 to about 1.2 equivalents, most preferably about 0.5 to about 1.0 equivalents are added;
(c) an additional about 0.9 to about 1.1 equivalents of the non-nucleophilic strong base, preferably about 1.0 equivalents are added to the mixture from step (b) while maintaining the temperature at about 0° C. to about 10° C., preferably about 0° C. to about 8° C.; and
(d) the temperature of the mixture from step (c) is raised to about 10° C. to about 50° C., preferably about 15 to about 45° C., more preferably about 15 to about 40° C. and an additional about 1.0 to about 1.5 equivalents of the non-nucleophilic strong base, preferably about 1.1 to about 1.4 equivalents are added while maintaining the temperature at about 10° C. to about 50° C., preferably about 15 to about 45° C., more preferably about 15 to about 40° C.

The enantioselective alkylation process of this invention is preferably carried out in an inert organic solvent. Suitable inert organic solvents, include, but are not limited to non-protic organic solvents, e.g., toluene, benzene, cyclohexane, tetrahydrofuran, anisole, chlorobenzene, and mixtures thereof. Toluene and ethylbenzene or a mixture of the two are preferred solvent. In the mixture case, the v/v ratio of toluene to ethylbenzene ranges from 1:5 to 1:1, preferably 1:2.

In a preferred embodiment of the enantioselective alkylation step for the preparation of the compound of formula of VI, the chiral amino alcohol is quinine, the non-nucleophilic lithium base is lithium di-isopropyl amide (LDA), normally as the LDA-mono(tetrahyrofuran) complex in a hydrocarbon solvent, e.g., cyclohexane or ethylbenzene, the organic amine or ether additive is 2-isopropylaniline (about 2 equivalents) or a 3:1 mixture of N-phenyl, N-benzyl amine and TMEDA, the solvent is toluene, and water is added after the first addition of LDA; about 2.0 to about 3.0 additional equivalents of LDA (as LDA-THF) are added in two equal portions. See Table in Comparative Example 8. When a mixture of two organic amine or organic ether additives, or a mixture of an organic amine and organic ether additive is used, the ratio of the additives in the mixture are in the range of about 1:4 to about 4:1 equivalents, preferably about 1:3 to about 3:1 equivalents.

In a preferred embodiment of the enantioselective alkylatine step, to a mixture of 1.0 equivalent of compound V, 1.2 equivalents of compound X, 2.1 equivalents of quinine, and 2.0 equivalents of 2-isopropylaniline, there is sequentially added 2.1 equivalents of LDA-THF (1 to 2 molar in ethylbenzene), 0.7 equivalents of water, and 0.7 equivalents of LDA-THF. The temperature of the so-formed reaction mixture is adjusted to between 15° and 40° C., and a third portion of 1.3 equivalents of LDA-THF is added over a period of 4 to 10 hours. The enantioselectivity of the free base of the compound of formula VI obtained from the preferred method ranges from 78 to 89% e.e. The enantioselectivity of the free base VI can be further enhanced by crystallization of the acid addition salt formed by contacting the free base VI with at least one equivalent of a chiral acid, such as N-α-t-Boc-L-asparagine or N-acetyl-L-phenylalanine.

In a more preferred embodiment of the enantioselective alkylation step, 1.0 equivalent of the LDA-TDF in ethylbenzene is pre-mixed with 0.5 equivalents of isopropylaniline. To a mixture of 1.0 equivalent of compound V, 1.1 equivalents of compound X, and 1.5 equivalents of quinine, there is sequentially added 2.1 equivalents of the LDA-THF/2-isopropylaniline base complex, 0.7 equivalents of water, and 0.7 equivalents of LDA-THF/2-isopropylaniline base complex. The temperature of the mixture is adjusted to between 15° to 40° C., and a third portion of 1.3 equivalents of LDA-THF/2-isopropylaniline base complex is added of 3 to 10 hours. The ee % of the free base of the compound of formula VI obtained from this more preferred method ranges from 88 to 92% ee. The enantioselectivity of the free base VI, can be further enhanced by crystallization of acid addition salt formed by contacting the free base VI with at least one equivalent of a chiral acid such as N-α-t-Boc-L-asparagine or N-acetyl-L-phenylalanine. This more preferred method using the LDA-THF/isopropylaniline base complex is a more robust process, provides a better control in maintaining lower impurities, and employs lower amounts of the compound X and of the LDA-THF/isopropylaniline base complex in the third addition.

The process of our invention is economical, because the chiral amino alcohol can be recovered and recycled for further use. For example, after the reaction is judged to be complete by HPLC, the reaction mixture can be quenched by adding water, and stirred at a temperature of about 0° C. to about 5° C. to precipitate the chiral amino alcohol, which can be recovered by filtration.

Triple Reduction & Bromination Steps:

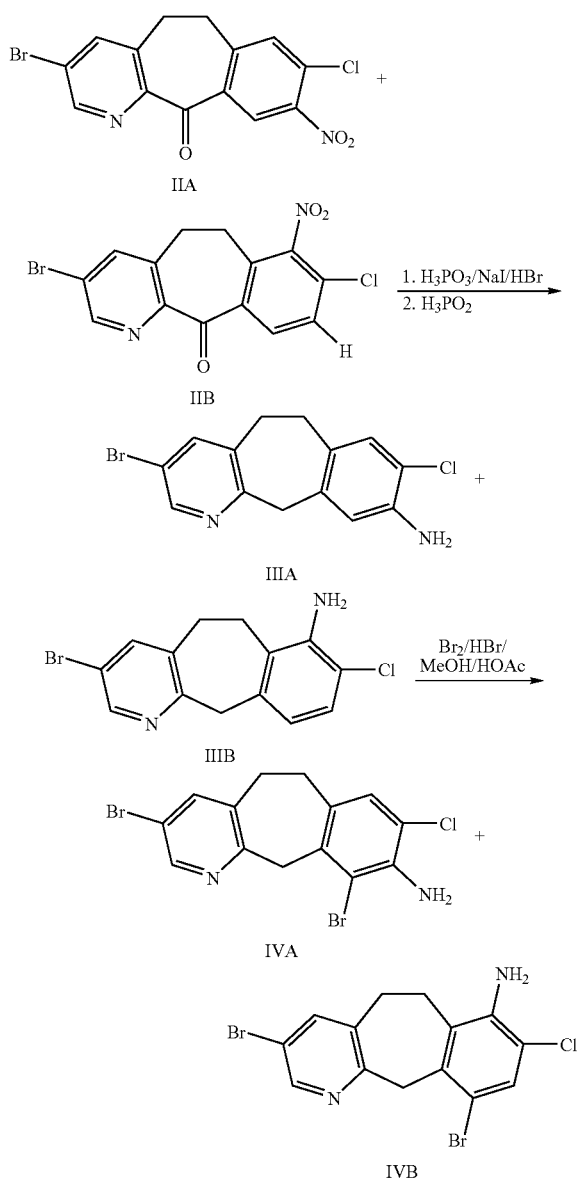

The present invention provides a novel triple reduction process for the conversion of compound II (normally as a mixture of isomers IIA & IIB) to compound III (normally as a mixture of isomers IIIA & IIIB). The triple reduction refers to the reduction of the nitro group of II to the corresponding amino group, the reduction of the ketone group to a hydroxy, and reduction of the hydroxy to the methylene group. The use of phosphorous acid ($H_3PO_3$), or hypophosphorous acid ($H_3PO_2$), or a combination of the two acids, and NaI for the reduction of nitro to amino group has not been reported. This combination for the reduction of aromatic ketone is superior to the reported method (*Tetrahedron Letters*, 2000, 41, 7817; *J. Org. Chem.* 1993, 58, 7149) where hazardous elemental phosphorous is used as a reagent.

Two alternative processes for the conversion of compound II to compound IV were developed. The first one is called two-pot process in which the triple reduction product, compound III, is isolated as a mixture of isomers IIIA & IIIB, and a bromination reaction is carried out in a separate step to afford compound IV which is isolated as a mixture of isomers, the 9-amino-isomer IVA and the 7-amino-isomer IVB. The second process combined the two steps into a one-pot reaction to produce compound IV (as a mixture of isomers IVA and IVA) directly from II (as a mixture of isomers IIA & IIB), without isolating III (as a mixture of isomers IIIA & IIIB). The compound II was prepared by nitration of compound XIII prepared as described in U.S. Pat. No. 6,307,048:

In the triple reduction step, the equivalent amount of phosphorous acid used ranged from about 2 to about 8 equivalents, preferably, about 3.5 to about 4.5 equivalents.

The catalytic amount of alkali iodide, e.g., NaI or KI, preferably NaI, or iodine ranged from about 0.01 to about 4 equivalents, preferably, about 0.05 to about 0.15 equivalents. The use of an alkali iodide is preferred; the use of sodium iodide (NaI) is more preferred.

The equivalent amount of hydrobromic acid ranged from about 6 to about 32 equivalents, preferably, about 13 to about 19 equivalents.

The equivalent amount of hypophosphorous acid ranged from about 1 to about 5 equivalents, preferably, about 2 to about 3 equivalents.

The triple reduction is carried out at a temperature range of about 50° to 120° C.; preferably at a temperature range of about 100° to 110° C.

The triple reduction is conducted under an inert atmosphere, preferably under nitrogen in an aqueous solvent mixture of the reagents.

In the bromination step, the solvent is a mixture of a $C_1$-$C_3$ alcohol and a $C_1$-$C_6$ alkananoic acid; preferably a mixture of methanol and acetic acid, or of ethanol and acetic acid.

In the two pot process, the equivalent amount of bromine ranged from about 1 to about 5 equivalents, preferably about 1.5 to about 2.5 equivalents, most preferably about 1.0 to about 1.05 equivalents.

In the one pot process, the equivalent amount of bromine ranged from about 1 to about 5 equivalents, preferably about 1.5 to about 2.0 equivalents, most preferably about 1.8 to about 2.5 equivalents.

The bromination was conducted at a temperature range of about 0° to about 40°, preferably about 10° to about 40° C.

Nitration Step:

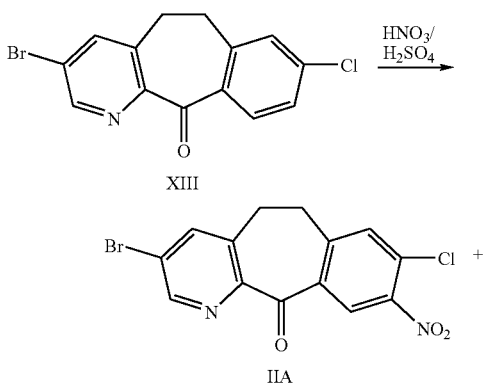

-continued

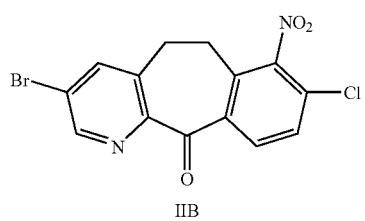

IIB

Nitration of XIII provides a mixture of the major isomer, the 9-nitro isomer IIA and the minor one, the 7-nitro isomer IIB. The mixture of IIA and IIB was used in the triple reduction step.

Deamination Step

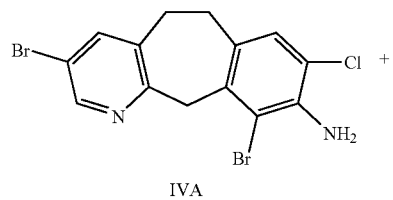

IVA

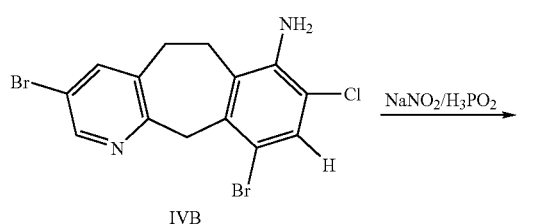

IVB

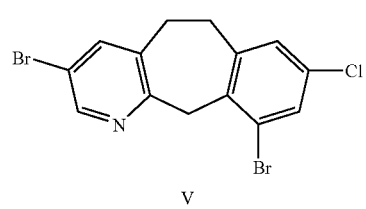

V

The amino groups in compound IV (as a mixture of isomers IVA and IVB) are removed with nitrous acid formed by the action of sodium nitrite ($NaNO_2$), with sulfuric acid, to form a diazonium salt, and treatment of the diazonium salt with hypophosphorous acid ($H_3PO_2$) to form compound V.

Urea Formation Step

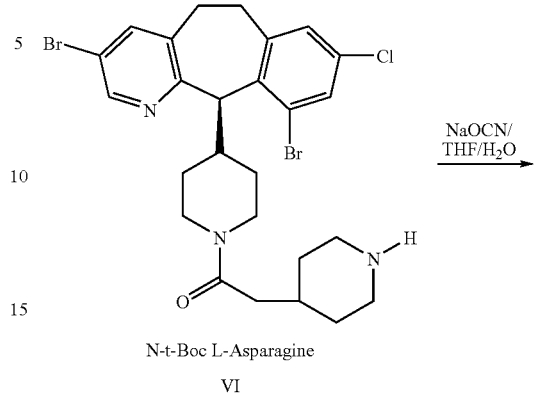

N-t-Boc L-Asparagine

VI

Crude I

Sodium isocyanate was found to be a better reagent for the ureanation of the compound VI than the commonly used urea reagent. This reagent requires lower reaction temperature and gives better impurity profile than urea used in previous process. The urea formation step was conducted at a temperature range of about 10° to about 60° C. in the presence of a water mixable organic solvent such as acetonitrile or tetrahydrofuran, preferably tetrahydrofuran containing about 40 to 60 volume % of water.

The equivalent amount of sodium cyanate (NaOCN) was about 1 to about 6 equivalents, preferably about 2.2 to 2.4 equivalents.

The equivalent amount of sodium carbonate ($Na_2CO_3$) was about 0 to about 1 equivalents, preferably about 0.1 to 0.3 equivalents.

Crude I was purified by adding it to a mixture of tetrahydrofuran:water (in a ratio of about 6:1, v/v) to form a suspension which was heated to temperature in the range of about 60° to 65° C. until a solution of volume A was formed. The so-formed solution was filtered, and approximately an equal volume of ethyl acetate was added. The so-formed solution was concentrated by distillation at atmospheric pressure. Approximately equal volume of ethyl acetate was added to the hot organic solution, and the so-formed solution was concentrated to approximately volume A by distillation at atmospheric pressure. The resulting solution was cooled to a temperature of about 20° to 25° C. over a period of about 1 hour, and the cooled solution was stirred at a temperature of about 20° to 25° C. for an additional 1 hour. The resulting solid was recovered by filtration, and dried, preferably in a vacuum oven at about 55° to 65° C. to produce compound I in a substantially chemically pure form, i.e., containing less 3% of impurities, preferably less than 1% of impurities.

Scheme 1 displays a preferred embodiment of the process of the invention. Compounds II, III, and IV are normally present as a mixture of the 7- and 9-isomers of each compound.
Scheme 1.
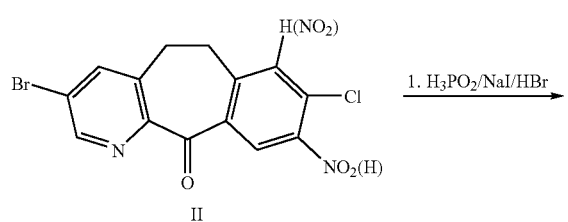
II
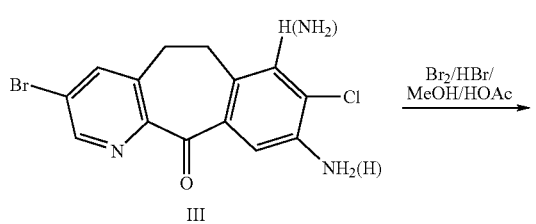
III
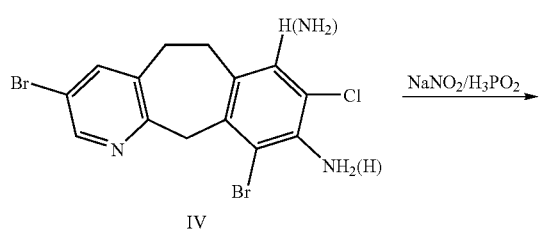
IV
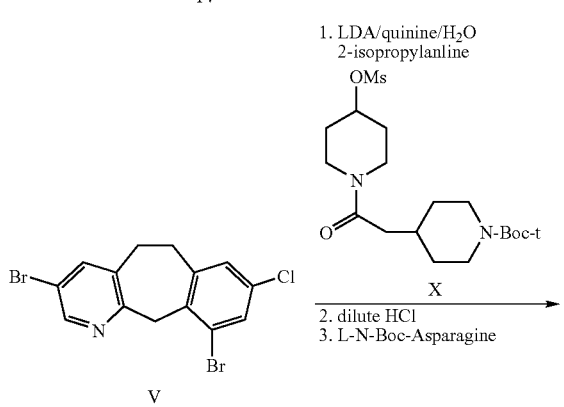
V
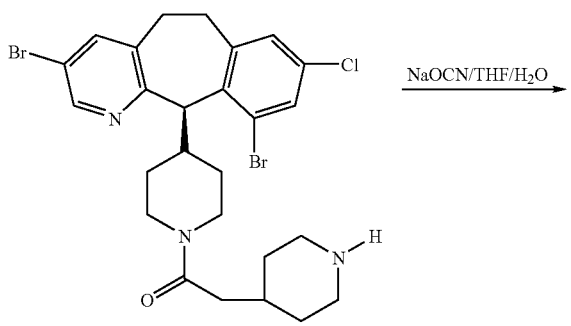
N-Boc-Asparagine
VI
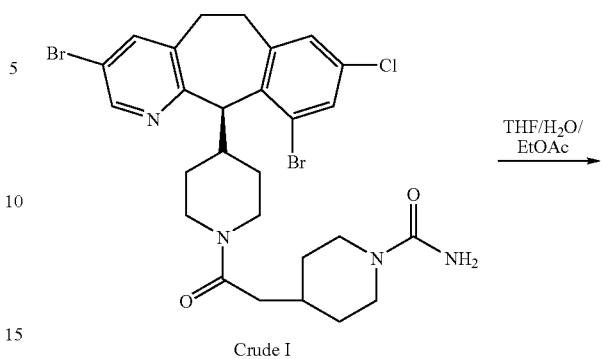
Crude I
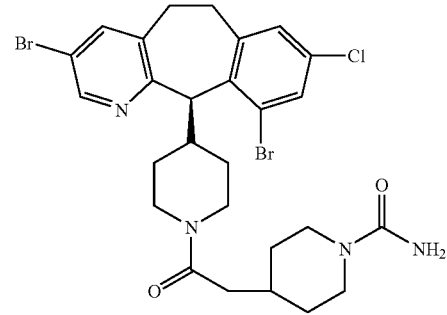
I
EXAMPLE 1
Preparation of Compound III (A Mixture of Isomers IIIA & IIIB)
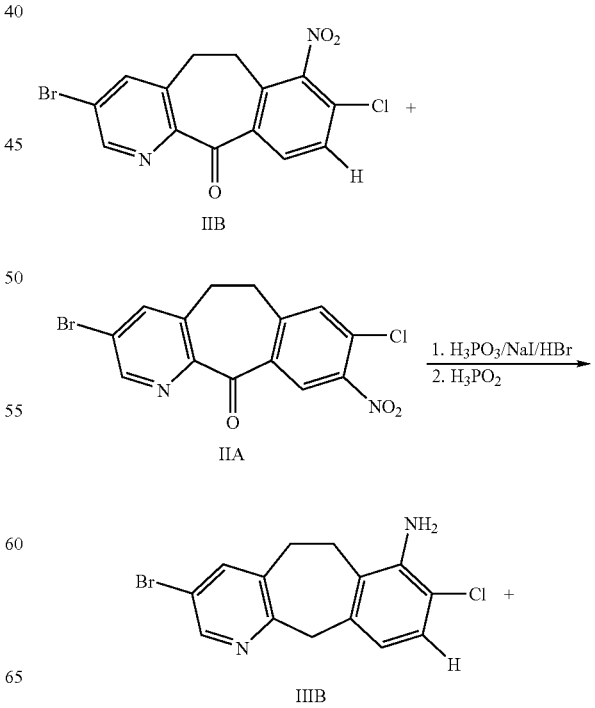
IIIB

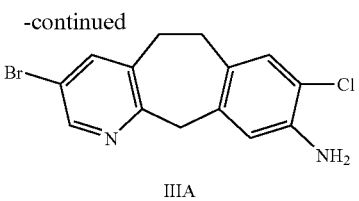

IIIA

To a 1 L three-neck flask equipped with a mechanical stirrer, a thermometer and a condenser were charged, under nitrogen, 50.0 g (0.14 mol) compound II (prepared in accordance with the procedures disclosed in col. 12, line 20 to col. 3, line 49 of U.S. Pat. No. 6,307,048) 2.0 g of sodium iodide (13.3 mmol), 45.0 g of phosphorous acid, $H_3PO_3$, (0.55 mol). To the mixture were added 250 mL of hydrobromic acid (48%) and 50 mL of water. The resulting suspension was heated to 107-111° C. and stirred at this temperature for a period of 4 hrs. The reaction mixture was then cooled to 60° C. and 40 mL (0.30 mol) of hypophosphorous acid, $H_3PO_2$, (50%) was added. The reaction mixture was heated to 100-110° C. and stirred at this temperature for a period of 6 hrs. The reaction mixture was cooled to 20° C. and was slowly transferred into a solution of 200 mL of ammonium hydroxide and 100 mL of methanol while maintaining the temperature under 30° C. The pH was adjusted to 5.0 with ammonium hydroxide and the suspension was stirred for 1 h at room temperature. The solid was filtered and washed with 50 mL of water. Drying the solid in a vacuum oven at 60° C. for 20 hrs gave 46.9 g of III as a mixture of a pair of isomers in about 70:30 ratio of IIIA:IIIB ratio (9 isomer:7 isomer) with 94% HPLC purity and 99% yield. 9-amino-isomer, IIIA, (major): $^1$H NMR (DMSO-$d_6$) 8.34 (d, J=2.3 Hz, 1H), 7.77 (d, J=2.3 Hz, 1H), 7.00 (s, 1H), 6.66 (s, 1H), 5.14 (s, 2H), 4.10 (s, 2H), 3.05-3.02 (m, 2H), 2.97-2.93 (m, 2H). $^{13}$C NMR (DMSO-$d_6$) 156.5, 146.7, 143.0, 140.1, 136.9, 136.8, 129.6, 127.6, 118.2, 116.2, 115.6. 7-amino-Isomer, IIIB: $^1$H NMR (DMSO-$d_6$) 8.35 (d, J=2.3 Hz, 1H), 7.87 (d, J=2.3 Hz, 1H), 7.00 (d, J=8.1 Hz, 1H), 6.49 (d, J=8.1 Hz, 1H), 5.06, (s, 2HO, 4.18 9s, 2H), 3.15-3.12 (m, 2H), 2.89-2.86 (m, 2H). $^{13}$C NMR (DMSO-$d_6$) 157.8, 146.9, 142.5, 139.0, 137.1, 135.9, 126.6, 123.3, 118.9, 118.4, 116.7, 42.4, 29.4, 26.7.

EXAMPLE 2

Preparation of Compound IV (A Mixture of Isomers IVA & IVB)

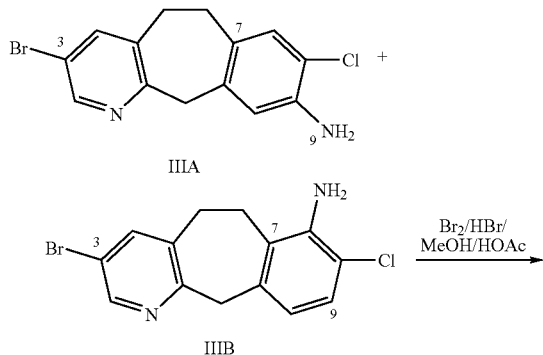

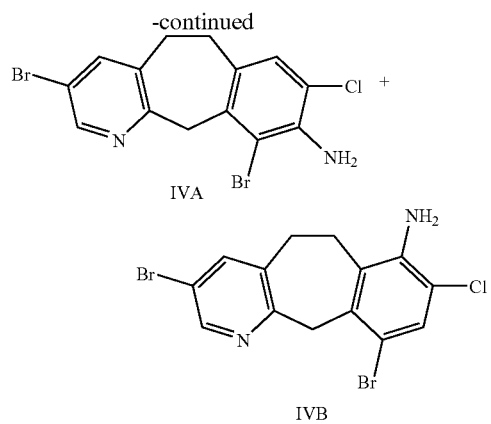

To a suspension of 30.0 g of compound III (as a mixture of IIIA & IIIB) from Example 1 (HPLC purity: 94%, 87.1 mmol) in 90 mL of methanol and 30 mL of acetic acid was added 15 mL of a solution of hydrobromic acid (48%) while maintaining the temperature between 10 to 20° C. To the resulting solution was added 4.5 mL of bromine (87.1 mmol) was added to the solution portion wise at a temperature between 15 and 20° C. The reaction mixture was stirred at ambient temperature for 1 h and was then poured into a solution of 6.0 g of sodium thiosulfate pentahydrate in 150 mL of water and 60 mL of ammonium hydroxide at a temperature between 10 and 20° C. The resulting suspension was heated to 40° C. and was stirred for 1 h while the temperature was allowed to return to 20° C. The solid was filtered, washed with 30 mL of water and dried in a vacuum oven at 60° C. to give 33.3 g of compound IV (as a mixture of isomers IVA & IVB) with a HPLC purity of 94% and 89.0% yield). For NMR see example 3.

EXAMPLE 3

One-Pot Process for Preparation of Compound IV (as a mixture of isomers

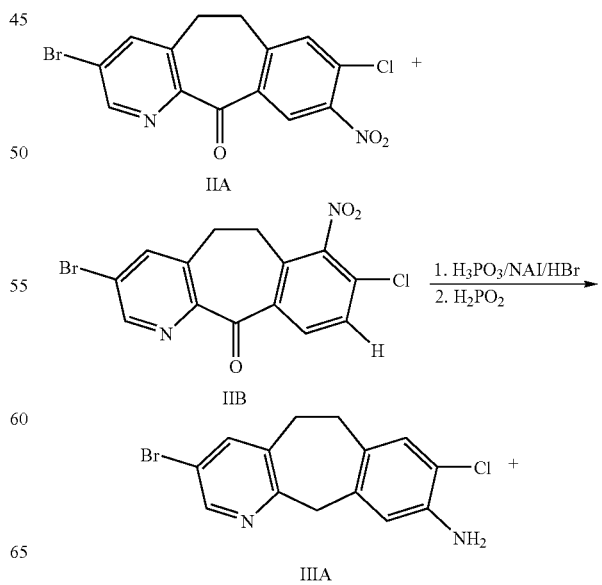

-continued

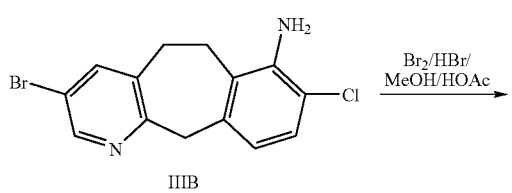

IIIB

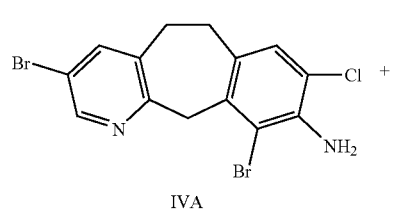

IVA

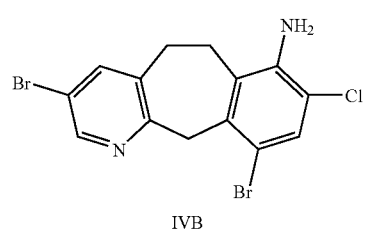

IVB

A mixture of compound II (as a mixture of isomers IIIA & IIB from Example 1) (10 g, 27.2 mmole), phosphorous acid, $H_3PO_3$, (9 g, 109.8 mmol), sodium iodide (0.4 g, 2.7 mmole), hydrobromic acid (48%) (50 mL) and water (10 mL) was stirred and heated at 105° C. for 6 hours and cooled to about 100° C. Hypophosphorous acid, $H_3PO_2$, (50%) (8 mL, 60.6 mmole) was added to the solution, which was then heated at 110° C. for about 6 hrs until the reaction is judged complete by HPLC. The solution was cooled to about 90° C. and acetic acid (20 mL) and ethanol (50 mL) were added and the solution continued to cool to 15° C. Bromine (3.3 mL, 63.9 mmole) was dropped into the mixture at a temperature between 15 to 20° C. and the mixture was stirred for another one hour. Ammonium hydroxide (25%) (60 mL) was slowly added to the mixture at a rate to keep the temperature below 50° C. After the ammonium hydroxide was added, the mixture was held at 50° C. for one hour. After cooled to 25° C., the mixture was filtrated. The solid was collected and treated as a slurry in water (150 mL) at 50° C. and collected again by filtration. The yield of IV is 10.3 g (93% yield). $^1$H NMR (DMSO-$d_6$): major product (9-amino-isomer IVA) 8.55 (d, J=2.3 Hz, 1H), 7.92 (d, J=2.3 Hz, 1H), 7.41 (s, 1H), 5.45 (s, 2H), 4.70 (s, 2H), 3.10-3.30 (m, 4H). Minor product (7-amino-isomer IVB) 8.58 (d, J=2.1, 1H), 7.99 (d, J=2.1, 1H), 7.55 (s, 1H), 5.60 (s, 2H), 4.69 (s, 2H), 3.10-3.30 (m, 4H).

EXAMPLE 4

Deamination Step

Preparation of Compound V

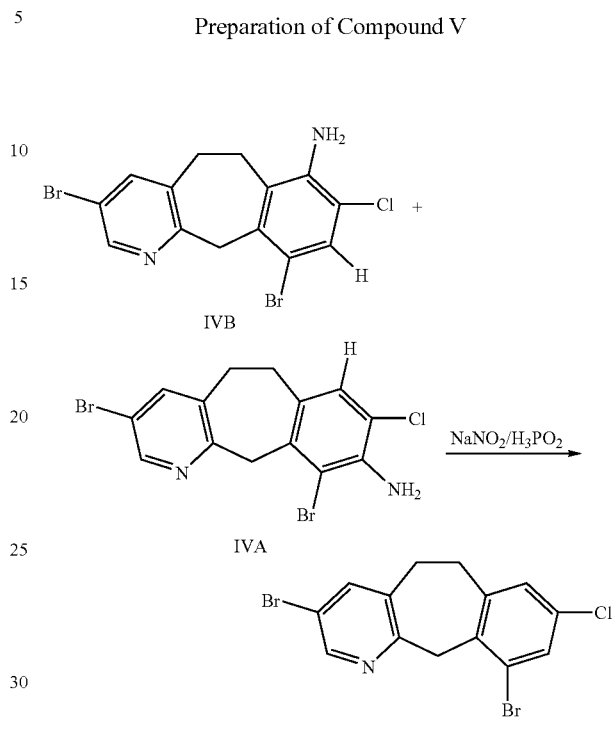

To a vigorously stirred suspension of 100.0 g mixture (93.0% purity, 0.231 mol) of compound IV as a mixture of isomers IVA & IVB from Example 3 in 200 mL of water at between 5 and 10° C. under sweeping nitrogen was added 300 mL of 98% sulfuric acid solution while allowing the internal temperature to rise to between 60 and 65° C. The resulted brown thick solution was cooled to between 5 and 10° C. Hypophosphorous acid (400 mL, 50% $H_3PO_2$ in water, 3.85 mole) was added followed by a solution of sodium nitrite (20.3 g, 0.286 mole) in 100 mL of water while maintaining the temperature between 10 and 20° C. After addition of sodium nitrite, 1.25 mL of Antifoam B silicone emulsion (J. T. Baker) was added. The reaction mixture was warmed to between 20 and 25° C., held for 2 hour, further heated to between 40 and 45° C. over a period of 2 hours and held for 4 hours. Upon the reaction completion, the resulted slurry was cooled to between −5 and 5° C., held for 6 hrs and filtered. The cake was washed with 200 mL of 30% aqueous sulfuric acid solution and dissolved into 1.5 L of a deoxygenated methanol solution containing 1% water, 1% sulfuric acid and 1.3% hypophosphorous acid between 50 and 60° C. To the resulted brown solution was added 10 g of activated carbon (Nuchar SN). After 30 minutes, the mixture was filtered through a half-inch pad of Celite between 50 and 60° C. The filtrate was heated to between 50 and 60° C. and slowly neutralized with 300 mL of a 2:1 solution of triethylamine (1.42 mole) and methanol until the solution pH value higher than 9 (on a water wet pH paper). The resulted slurry was cooled to between 0 and 5° C. in a period of 1 hour, held for 2 hours and filtered. The cake was washed with methanol, dried at 60 and 65° C. under vacuum and gave 73 g of compound V, 8-chloro-3,10-dibromo-5,6-dihydro-11H-benzo[5,6]cycloheptal-[1,2-b]pyridine, as a light yellow solid in 82% yield; m.p. 163-164° C. $^1$H NMR (CDCl$_3$): δ 8.38 (d, J=2.0 Hz, 1H), 7.46 (d, J=2.0 Hz, 1H), 7.44 (d, J=2.0 Hz, 1H), 7.14 (d, J=2.0 Hz, 1H), 4.45 (s, 2H), 3.10-3.20 (m, 4H), $^{13}$C NMR (CDCl$_3$): δ 154.1, 148.5, 143.9, 141.7, 137.2, 135.8, 133.9, 131.6, 128.7, 125.5, 119.8, 41.7, 32.9, 32.7. Anal. Calcd for C$_{14}$H$_{10}$Br$_2$ClN: C, 43.37; H, 2.58; N, 3.61; Br, 41.31; Cl, 9.17; Found: C, 43.33; H, 2.66; N, 3.69; Br, 41.06; Cl, 9.11.

EXAMPLE 5

Chiral Alkylation Step

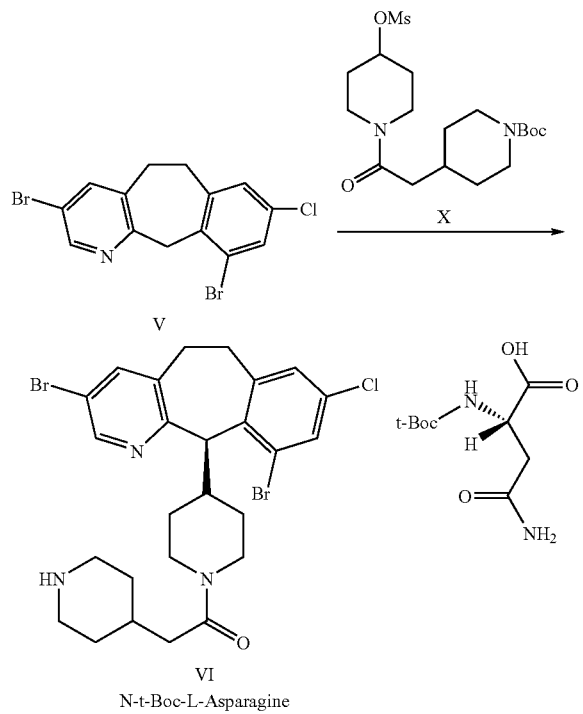

N-t-Boc-L-Asparagine

To a mixture of quinine (175.0 g, 539.4 mmol, 2.1 molar equivalents), 8-chloro-3,10-dibromo-6,11-dihydro-5H-benzo [5,6] cyclohepta[1,2-b]pyridin-11-yl (compound V, 100.0 g, 258.1 mmol, 1.0 molar equivalents obtained from Example 4), and 1-(N-[(tert-butyloxy)carbonyl]-4-piperidinyl)acetyl-4-mesyloxy-piperidine (X, 125.0 g, 309.0 mmol, 1.2 molar equivalents) from Example 4 suspended in a mixture of ethylbenzene (600 mL) and toluene (400 mL) is added 2-isopropylaniline (73.1 mL, 70.8 g, 523.9 mmol, 2.0 molar equivalents). The resulting suspension is degassed and purged with nitrogen three times to remove any dissolved oxygen. While maintaining the temperature of the mixture between 15° and 25° C., a solution of lithium diisopropylamide mono(tetrahydrofuran) complex in either ethylbenzene, cyclohexane, or toluene at a concentration of 1.0 to 2.2 molar is slowly added until the reaction mixture turns a deep red color (typically 539.4 mmol, 2.1 molar equivalents). Water (3.34 mL, 3.3 g, 185.8 mmol, 0.7 molar equivalents) is then added, and the reaction mixture turns from the deep red color to a yellow-orange color. Again while maintaining the temperature of the reaction mixture between 15° and 25° C., a second portion of the solution of lithium diisopropylamide mono(tetrahydrofuran) complex in either ethylbenzene, cyclohexane, or toluene at a concentration of 1.0 to 2.2 molar is slowly added until the reaction mixture returns to a deep red color (typically 185.8 mmol, 0.7 molar equivalents). The temperature of the mixture is then adjusted to between 15° and 40° C., and over a period of 4 to 10 hours, a third portion of the solution of lithium diisopropylamide mono(tetrahydrofuran) complex in either ethylbenzene, cyclohexanes, or toluene at a concentration of 1.0 to 2.5 molar is added (335.5 mmol, 1.3 molar equivalents). After stirring an additional hour between 15 and 40° C., the mixture is cooled to between 0 and 10° C., quenched by the addition of water (300 mL), and stirred for an additional 4 to 6 hours to precipitate the quinine. After filtration, the layers are separated, and the organic layer is washed with portions of 2N HCl until the pH is below 2.

While maintaining the temperature between 15° and 25° C., 6N HCl (400 mL) is added to the resulting organic layer. After stirring for one to two hours, the mixture is diluted with water (300 mL) and cooled to between 0° and 10° C. The layers are separated and the acidic aqueous layer containing the product is held between 0° and 10° C. The waste organic layer is neutralized with aqueous sodium bicarbonate and discarded.

In a separate reaction vessel, fresh toluene (1000 mL) and aqueous sodium hydroxide (450 mL of 25% w/v, or 270 mL of 40% w/v) are combined. The acidic aqueous product layer is then slowly added while maintaining the mixture temperature between 0 and 30° C. After checking the pH of the final mixture to make sure the pH is above 13, the mixture is maintained between 20° and 25° C. for an additional hour. The layers are separated, and the organic phase which now contains the product is washed with a dilute potassium carbonate solution (500 mL of 5% w/v) and separated. The organic phase is concentrated under vacuum to approximately 500 mL. In a separate reaction vessel, N-α-t-Boc-L-Asparagine (56.0 g, 241.2 mmol, 0.9 molar equivalents) is suspended in a mixture of toluene (582 mL) and methyl alcohol (48 mL). The slurry is heated to between 55 and 65° C. A portion of the concentrated product (VI) solution (7 to 20%) is transferred over 30 minutes to the warm N-α-t-Boc-L-Asparagine slurry. In a separate vessel, a slurry of a previous sample of the product (VI, N-α-t-Boc-L-Asparagine) (1.8 g, 2.17 mmol, 0.008 molar equivalents) in toluene (20 mL) is prepared, then transferred into the warm N-α-t-Boc-L-Asparagine slurry. The remainder of the concentrated product (VI) solution (80 to 93%) is added over 2 hours to the crystallization mixture, while maintaining the temperature between 55 and 65° C., during which time the product crystallizes from the mixture. A rinse of toluene (50 mL) follows the concentrated product (VI) solution. The mixture is held at 55 to 65° C. for an additional 30 minutes, then cooled to between 20° and 25° C. for one hour. The product (VI, N-α-t-Boc-L-Asparagine) is isolated by filtration and washed with toluene (600 mL). After drying, typical yields are 75 to 82% with ee values from 98.0 to 99.5% ee. $^1$H NMR (400 MHz, CDCl$_3$): 6 (ppm) 9.58 (bs, 1H), 8.41 (s, 1H), 7.52 (t, J=2.8 Hz, 1H), 7.47 (t, J=2.0 Hz, 1H), 7.11 (t, J=2.6 Hz, 1H), 6.81 (bs, 1H), 6.30 (bs, 1H), 5.92 (d, J=6.4 Hz, 1H), 4.86 (dd, J$_1$=5.5 Hz, J$_2$=10.3 Hz, 1H), 4.53 (m, 1H), 4.18 (m, 1H), 3.80 (t, J=13.8 Hz, 1H), 3.59 (tt, J=4.6 Hz, J$_2$=13.8 Hz, 1H), 3.37 (m, 2H), 3.24 (dt, J=4.2 Hz, J$_2$=17.6 Hz, 1H), 2.95 (t, J=15.8 Hz, 1H), 2.79 (m, 5H), 2.66 (dd, J$_1$=4.1 Hz; J$_2$=14.7 Hz, 1H), 2.36 (m, 2H), 2.25 (t, J=6.2 Hz, 2H), 2.07 (bs, 1H), 1.85 (m, 2H), 1.39 (m, 16H).

EXAMPLE 6

Preparation of I (Crude)

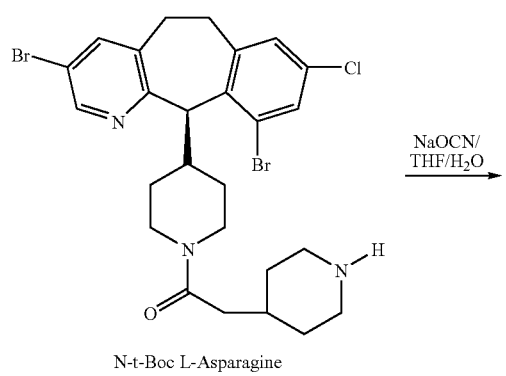

N-t-Boc L-Asparagine
VI

To a mixture of VI N-t-Boc L-asparagine salt (10 g, 12.1 mmol) from Example 5, NaOCN (1.8 g, 27.7 mmol), Na$_2$CO$_3$ (0.3 g, 2.4 mmol), and tetrahydrofuran (THF) (40 mL) was added water (20 mL) at 20 to 25° C. The resultant suspension was stirred for 4 hr at 40 to 50° C. until reaction is completed n-Butanol (n-BuOH) (50 mL) and water (50 mL) were added to the solution and the mixture was cooled to 20 to 25° C. The mixture was stirred for 10 minutes. The aqueous layer was separated and re-extracted with n-BuOH (30 mL). The combined organic layer was washed with water twice. The organic layer was treated with Darco at 40° C. After filtration, the organic solution was concentrated under vacuum to 30 mL and methyl t-butyl ether (70 mL) was added and the mixture was cooled to 0 to 5° C. for crystallization. The solid was collected through filtration and dried to give 7.3 g of crude 1 (95% yield). Mp. 222-223° C.

EXAMPLE 7

Crystallization of Crude I

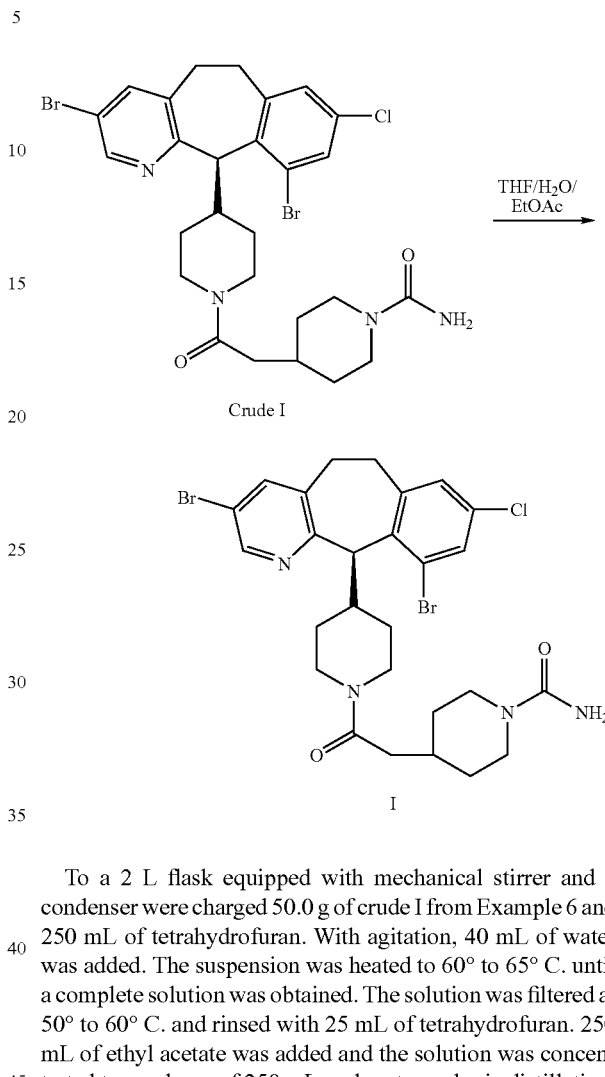

To a 2 L flask equipped with mechanical stirrer and a condenser were charged 50.0 g of crude I from Example 6 and 250 mL of tetrahydrofuran. With agitation, 40 mL of water was added. The suspension was heated to 60° to 65° C. until a complete solution was obtained. The solution was filtered at 50° to 60° C. and rinsed with 25 mL of tetrahydrofuran. 250 mL of ethyl acetate was added and the solution was concentrated to a volume of 250 mL under atmospheric distillation. 200 mL of ethyl acetate was added and the mixture was concentrated to a volume of 250 mL under atmospheric pressure. The mixture was cooled to 20° to 25° C. over a period of 1 h, then stir at 20° to 25° C. for 1 h. The resulting solid was filtered, washed with 25 mL of ethyl acetate and dried in a vacuum oven at 55° to 65° C. to give 48.0 g (96% yield, >99% chemically pure and >98% ee) of compound I. $^1$H NMR (CDCl$_3$) δ 8.38 (d, J=2.2 Hz, 1H), 7.48 (dd, J=4.8, 2.0 Hz, 1H), 7.43 (d, J=2.0 Hz, 1H), 7.08 (d, J=2.2 Hz, 1H), 4.82, (dd, J=10.3, 4.2 Hz, 1H), 4.53, (t, J=7.4 Hz, 1H), 4.34 (s, 2H), 3.90-3.70 (m, 3H), 3.55 (tt, J=13.8, 4.3 Hz, 1H), 3.20 (dt, J=17.6, 4.2 Hz, 1H), 2.95-2.82 (m, 1H), 2.80-2.70 (m, 4H), 2.37-2.30 (m, 2H), 2.20-2.15 (m, 2H), 2.00-1.95 (m, 1H), 1.70 (d, J=12.8 Hz, 2H), 1.48-1.00 (m, 6H). $^{13}$C NMR (CDCl$_3$, two rotamers) 169.5, 158.3, 155.1, 155.0, 146.8, 144.1, 144.1, 137.8, 137.7, 136.3, 136.2, 132.4, 130.4, 129.8, 129.7, 126.7, 126.7, 118.8, 58.3, 58.2, 45.4, 45.3, 43.9, 41.4, 41.2, 40.8, 39.0, 38.9, 33.1, 32.7, 32.0, 31.8, 31.4, 31.3, 30.8, 30.6. Anal. Calcd for C$_{27}$H$_{31}$Br$_2$ClN$_4$O$_2$: C, 50.76; H, 4.89; N, 8.77. Found C, 50.84; H, 4.77; N, 8.73.

COMPARATIVE EXAMPLE 8

The procedure of Example 6 of U.S. Pat. No. 6,307,048 was followed except that the base was varied and an organic amino or ether additive listed in the table below was added during the enantioselective alkylation step. To a mixture of 1.0 equivalents of V, 1.2 equivalents of X, 2.1 equivalents of quinine and the organic amine or ether additive listed in the Table for Comparative Example 8, there was added sequentially, 2.1 equivalents of the LDA-THF (1-2 molar in ethyl benzene), 0.7 equivalents of water, and 0.7 equivalents of LDA-THF (1-2 molar in ethyl benzene). The temperature was adjusted to between 15° and 40° C. The t-Boc compound of formula VI was isolated and the % ee value was measured. The amount of organic additive was varied from 1 to 3 equivalents. The t-Boc protecting group could be removed by acid hydrolysis with, for example, 20% $H_2SO_4$ as described in Example 6 of U.S. Pat. No. 6,307,048 to form the free base, i.e., the compound of formula VI wherein $R_1$ is hydrogen. The enantioselectivity of the free base (reported in the Table below) can be further enhanced by crystallization of the acid addition salt formed by contacting the free base of the compound of formula VI with at least one equivalent of a chiral organic acid such as N-α-t-Boc-asparagine or N-acetyl-L-phenylalanine.

Table for Comparative Example 8

| Run | BASE | Organic Amine or Ether Additive | Amount of Additive (eq.) | ee %[3] | Yield |
|---|---|---|---|---|---|
| 1 | LDA[1] | None | 0 | 60-83 | 90% |
| 2 | LDA | t-BuOMe | 1 | 90 | 95% |
| 3 | Li N-butyl, N-phenylamide | TMEDA[2] | 1 | 90 | 88% |
| 4 | LDA | isopropylamine | 3 | 89 | 98% |
| 5 | LDA | 2-isopropyl-aniline | 2 | 88 | 97% |
| 6 | LDA | N-ethylaniline | 1 | 88 | 98% |
| 7 | LDA | N-phenyl, N-benzyl-amine/TMEDA | 3:1 | 91 | 93% |
| 8 | Li N-ethyl-phenylamide | N-phenyl, N-naphthyl amine | 1 | 96 | 86% |

Note:
[1] LDA = Lithium diisopropylamide.
[2] TMEDA = Tetramethylethylenediamine.
[3] ee % measured on free base of formua VI wherein $R_1$ is H.

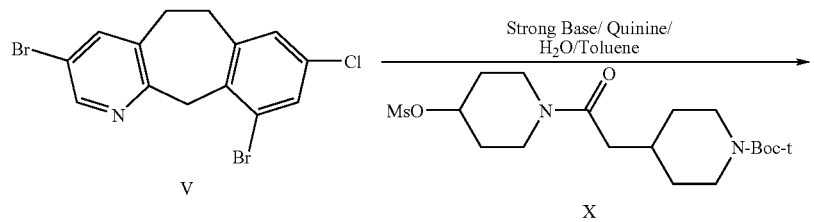

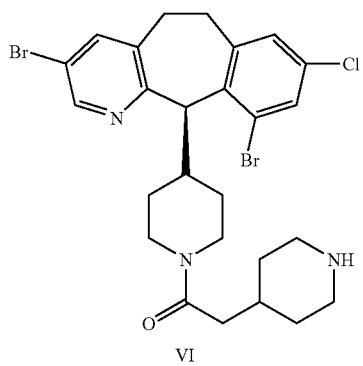

EXAMPLE 9

Enantioselective Alkylation with the LDA Mono(tetrahydrofuran)-2-Isopropylaniline Base Complex

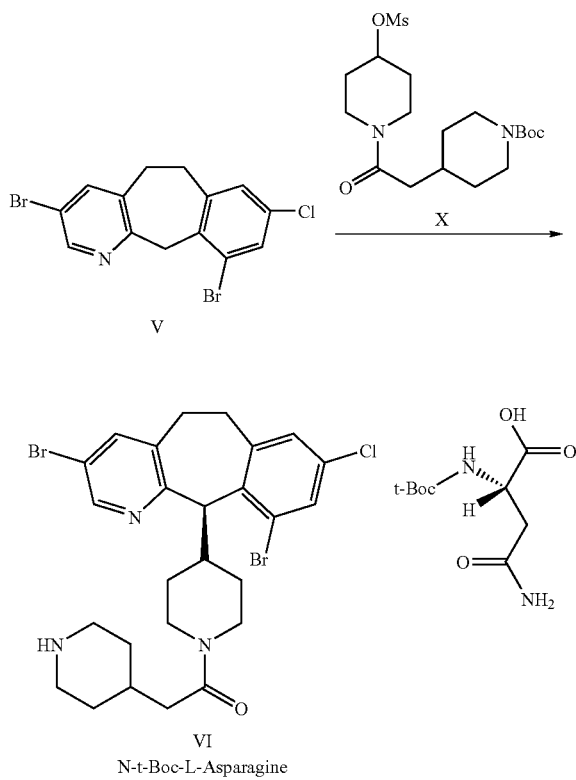

Preparation of the LDA-monoTHF/2-isopropylaniline Base Complex:

To a solution of LDA (lithium diisopropylamide mono (tetrahydrofuran) complex in toluene or cyclohexanes or ethylbenzene at a concentration of 1.0 to 2.2 mole) (169 ml at 2M concentration) at 0°-10° C. was added dropwise 2-isopropylaniline (23.4 ml, 180 mmole). The temperature was controlled under 20 to 25° C. during the addition. After the mixture is agitated for 10 minutes, it is ready for the following alkylation reaction.

Alkylation Reaction:

To a mixture of quinine (42.0 g, 129.5 mmol, 2.1 molar equivalents), 8-Chloro-3,10-dibromo-6,11-dihydro-5H-benzo [5,6] cyclohepta[1,2-b]pyridin-11-yl (V, 24.0 g, 61.9 mmol, 1.0 molar equivalents) (compound V), and 1-(N-[(tert-butyloxy)carbonyl]-4-piperidinyl)acetyl-4-mesyloxy-piperidine (X, 30.0 g, 74.2 mmol, 1.2 molar equivalents) are added ethylbenzene (144 mL) and toluene (96 mL). The resulting suspension is degassed and purged with nitrogen three times to remove any dissolved oxygen. While maintaining the temperature of the mixture between 15° and 25° C., a solution of LDA solution prepared above is slowly added until the reaction mixture turns a deep red color (74 ml, 2.1 molar equivalents). Water (0.8 mL, 44.4 mmol, 0.7 molar equivalents) is then added, and the reaction mixture turns from the deep red color to a yellow-orange color. Again while maintaining the temperature of the reaction mixture between 15° C. and 25° C., a second portion of the solution of LDA prepared above is slowly added until the reaction mixture returns to a deep red color (24 ml, 0.7 molar equivalents). The temperature of the mixture is then adjusted to between 15° and 40° C., and over a period of 2 to 10 hours, a third portion of the solution of LDA prepared above, is added (46 ml, 1.3 molar equivalents). After stirring an additional hour between 15 and 40° C., the mixture is cooled to between 0 and 10° C., quenched by the addition of water (75 mL), and stirred for an additional 4 to 6 hours to precipitate the quinine. After filtration, the layers are separated, and the organic layer is washed with portions of 2N HCl until the pH is below 2.

While maintaining the temperature between 15° and 25° C., 6N HCl (96 mL) is added to the resulting organic layer. After stirring for one to two hours, the mixture is diluted with water (72 mL) and cooled to between 0° and 10° C. The layers are separated and the acidic aqueous layer containing the product is held between 0° and 10° C. The waste organic layer is neutralized with aqueous sodium bicarbonate and discarded.

In a separate reaction vessel, fresh toluene (240 mL) and aqueous sodium hydroxide (108 mL of 25% w/v, or 65 mL of 40% w/v) are combined. The acidic aqueous product layer is then slowly added while maintaining the mixture temperature between 0° and 30° C. After checking the pH of the final mixture to make sure the pH is above 13, the mixture is maintained between 20° and 25° C. for an additional hour. The layers are separated, and the organic phase which now contains the product is washed with a dilute potassium carbonate solution (120 mL of 5% w/v) and separated. The organic phase is concentrated under vacuum to approximately 120 mL of a concentrated product (VI) solution. A sample of the free base (VI) is isolated from the concentrated product solution, and dried. The selectivity of the free base (VI) before salt formation ranges from 84 to 87% ee. In a separate reaction vessel, N-α-t-Boc-L-Asparagine (13.2 g, 57.9 mmol, 0.9 molar equivalents) is suspended in a mixture of toluene (155 mL) and methyl alcohol (8.7 mL). The slurry is heated to between 55 and 65° C. A portion of the concentrated product (VI) solution (7 to 20%) is transferred over 30 minutes to the warm N-α-t-Boc-L-Asparagine slurry. In a separate vessel, a slurry of a previous sample of the product (VI N-α-t-Boc-L-Asparagine) (0.4 g, 0.5 mmol, 0.008 molar equivalents) in toluene (5 mL) is prepared, then transferred into the warm N-α-t-Boc-L-Asparagine slurry. The remainder of the concentrated product (VI) solution (80 to 93%) is added over 2 hours to the crystallization mixture, while maintaining the temperature between 55 and 65° C., during which time the product crystallizes from the mixture. A rinse of toluene (2 mL) follows the concentrated product (VI) solution. The mixture is held at 55 to 65° C. for an additional 30 minutes, then cooled to between 20° and 25° C. for one hour. The product (VI N-α-t-Boc-L-Asparagine) is isolated by filtration and washed with toluene (144 mL). After drying, typical yields are 75 to 82%, and the selectivities range from 98.0 to 99.5% ee. $^1$H NMR (400 MHz, CDCl$_3$): 6 (ppm) 9.58 (1H, bs); 8.41 (1H, s); 7.52 (1H, t, J=2.8 Hz); 7.47 (1H, t, J=2.0 Hz); 7.11 (1H, t, J=2.6 Hz); 6.81 (1H, bs); 6.30 (1H, bs); 5.92 (1H, d, J=6.4 Hz); 4.86 (1H, dd, J$_1$=5.5 Hz, J$_2$=10.3 Hz); 4.53 (1H, m); 4.18 (1H, m); 3.80 (1H, t, J=13.8 Hz); 3.59 (1H, tt, J$_1$=4.6 Hz, J$_2$=13.8 Hz); 3.37 (2H, m); 3.24 (1H, dt, J$_1$=4.2 Hz, J$_2$=17.6 Hz); 2.95 (1H, t, J=15.8 Hz); 2.79 (5H, m); 2.66 (1H, dd, J$_1$=4.1 Hz; J$_2$=14.7 Hz); 2.36 (2H, m); 2.25 (2H, t, J=6.2 Hz); 2.07 (1H, bs); 1.85 (2H, m); 1.39 (16H, m).

What is claimed is:

1. A process for the preparation of a compound represented by formula V

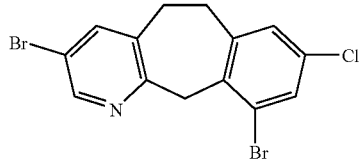

which comprises (1) contacting a compound represented by formula IIA

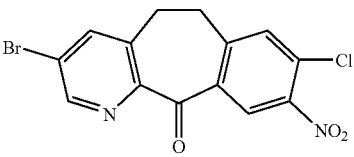

with at least about an equivalent amount of phosphorous acid in the presence of catalytic amount of an alkali iodide or iodine and hydrobromic acid in water to form a reaction mixture, and then adding to the reaction mixture at least about an equivalent of hypophosphorous acid to form a compound represented by formula IIIA

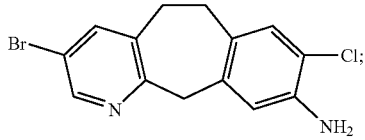

(2) contacting the resulting compound represented by formula IIIA with at least about an equivalent amount of bromine in the presence of an organic acid and a lower alkanol to form a compound represented by formula IVA

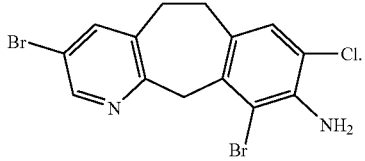

2. The process of claim 1 which further comprises the step of contracting the compound represented by formula IVA with at least about equivalent amount of hypophosphorous acid and the presence of sodium nitrite in a aqueous acidic medium to form the compound represented by formula V

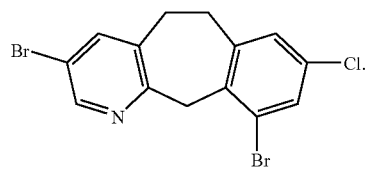

3. The process of claim 1 wherein a mixture a compound of IIA and a compound represented by formula IIB:

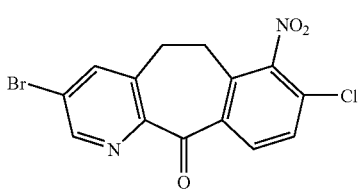

is present in the contacting step (1) and a compound represented by formula IVB

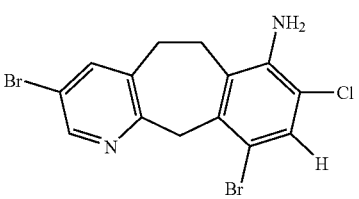

is also formed in step (2).

4. A process of preparing compounds represented by formulas IVA and IVB

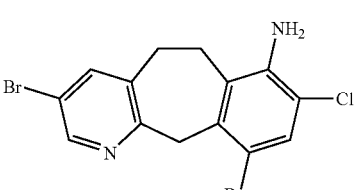

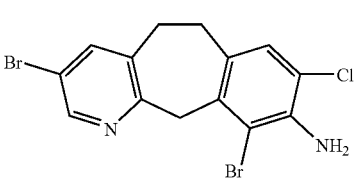

which comprises contacting compounds represented by formulas IIA and IIB

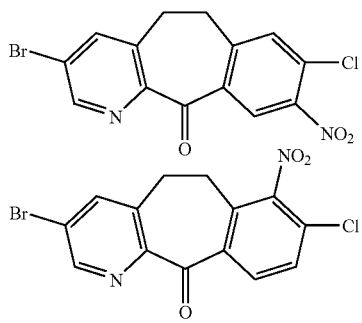

with at least about an equivalent amount of phosphorous acid in the presence of at least a catalytic amount of sodium iodide, hydrobromic acid, in water to form a reaction mixture and adding to the so-formed reaction mixture at least about an equivalent amount of hypophosphorous acid, and continuing the contacting for a time sufficient to form a reaction mixture comprising the compounds represented by formulas IIIA and IIIB, and contacting the resulting reaction mixture with at least about an equivalent of bromine in the presence of an organic acid and a lower alkanol to form a compound represented by formula form a mixture comprising the compounds represented by formulas IVA and IVB.

* * * * *

UNITED STATES PATENT AND TRADEMARK OFFICE
CERTIFICATE OF CORRECTION

| | | |
|---|---|---|
| PATENT NO. | : 7,582,763 B2 | Page 1 of 1 |
| APPLICATION NO. | : 11/287041 | |
| DATED | : September 1, 2009 | |
| INVENTOR(S) | : Frank Xing Chen et al. | |

It is certified that error appears in the above-identified patent and that said Letters Patent is hereby corrected as shown below:

In the Claims:

Claim 3, col. 34, lines 12 and 13, please correct "wherein a mixture a compound of IIA" to:

-- wherein a mixture of compound IIA --

Signed and Sealed this

Sixteenth Day of February, 2010

David J. Kappos
*Director of the United States Patent and Trademark Office*